US006472206B1

(12) United States Patent
Scholl et al.

(10) Patent No.: US 6,472,206 B1
(45) Date of Patent: Oct. 29, 2002

(54) IN SITU GROWTH, FREEZING AND TESTING OF CULTURED CELLS

(75) Inventors: David R. Scholl, Athens, OH (US); Francesco Saverio Ambesi-Impiombato, Udine (IT); James L. Brown, Athens, OH (US); Leonard D. Kohn, Athens, OH (US); Joseph A. Jollick, Jr., Athens, OH (US)

(73) Assignees: Interthyr Corporation, Athens, OH (US); Diagnostic Hybrids, Inc., Athens, OH (US)

( * ) Notice: Subject to any disclaimer, the term of this patent is extended or adjusted under 35 U.S.C. 154(b) by 0 days.

(21) Appl. No.: 09/560,548

(22) Filed: Apr. 28, 2000

(51) Int. Cl.$^7$ .............................. C12N 5/00; C12Q 1/00; C12Q 1/70
(52) U.S. Cl. ............................ 435/325; 435/1.3; 435/4; 435/5; 435/7.22; 435/374; 435/395; 435/404; 424/93.1
(58) Field of Search ...................... 435/1.3, 4, 5, 7.22, 435/325, 374, 395, 404; 424/93.1

(56) References Cited

U.S. PATENT DOCUMENTS

| | | | |
|---|---|---|---|
| 3,753,357 A | 8/1973 | Schwartz | 62/64 |
| 3,852,155 A | 12/1974 | Moore | 195/1.8 |
| 4,609,622 A | 9/1986 | Kohn et al. | 435/29 |
| 5,145,770 A | 9/1992 | Turbo et al. | 435/1 |
| 5,776,769 A | 7/1998 | Critser et al. | 435/307 |
| 5,869,243 A | * 2/1999 | Juaregui et al. | 435/6 |
| 5,935,855 A | 8/1999 | Impiobato et al. | 435/353 |
| 5,939,253 A | * 8/1999 | Scholl et al. | 435/5 |

OTHER PUBLICATIONS

Ohno et al., A simple method for in situ freezing of anchorage-dependent cells including rat liver parenchymal cells, Cytotechnology, vol. 5, pp. 273–277, 1991.*
Wiedbrauk and Johnston (1993) "Mammalian Cell Culture Procedures," in *Manual of Clinical Virology*, pp. 33–44, Raven Press, NY.
Leland (1996) "Modified Virus Isolation Systems," in *Clinical Virology*, pp. 79–90, W.B. Saunders Co., Philadelphia, PA.
Sambrook et al. (1989) in *Molecular Cloning: A Laboratory Manual*, Cold Spring Harbor Press, Plainview, NY, at pp. 16.9–16.15.
Freshney (1983) Culture of Animal Cells, A Manual of Basic Technique, Alan R. Liss, Inc., NY, pp. 189–198.
Hay, "Cell line preservation and characterization," in *Animal Cell Culture, A Practical Approach, Second Edition*,, Oxford University Press, Oxford, Freshney, ed., 1992, pp. 95–148.
Lo et al. (1999) "Fluorescence In Situ Hybridization (FISH) Screening of Frozen Cell Lines in Large Numbers," BioTechniques 26:408–412.
Isozaki et al. (1987) "Control of c–fos and c–myc proto–oncogene induction in rat thyroid cells in culture," Molec. Endocrinol. 1(11):839–848.
Smith et al. (1986) "The influence of oxygen tension on the long-term growth in vitro of haematopoietic progenitor cells from human cord blood," British J. Haematol. 63:29–34.
Bellur et al. (1990) "Repeatedly passed FRTL–5 rat thyroid cells can develop insulin and insulin-like growth factor–I–sensitive cyclooxygenase nd prostaglandin E2 isomerase–like activities together with altered basal and thyrotropin–responsive thymidine incorporation into DNA," Endocrinology 127(3):1526–1540.
Vitti et al. (1982) "Graves' IgG stimulation of continuously cultured rat thyroid cells: a sensitive and potentially useful clinical assay," J. Endocrinol. Invest. 5:179–182.
Colinas et al. (1994) "In vitro effects of hydroquinone, benzoquinone and doxorubicin on mouse and human bone marrow cells at physiological oxygen partial pressure," Toxicol. Appl. Pharmacol. 129(1):95–102.
Rich et al. (1986) "A role for the macrophage in normal hemopoiesis. II. Effect of varying physiological oxygen tensions on the release of hemopoietic growth factors from bone–marrow–derived macrophage in vitro," Exp. Hematol. 14:746–751.

* cited by examiner

Primary Examiner—Hankyel T. Park
Assistant Examiner—Stacy S. Brown
(74) Attorney, Agent, or Firm—Medlen & Carroll LLP

(57) ABSTRACT

The present invention provides methods and compositions for the in situ growth, freezing and testing of cultured cells. In particular, the present invention provides methods and compositions for the long-term preservation of cells in ready-to-use formats for testing. In addition, the present invention provides rapid and easy to use means to diagnose viral and other infections. Furthermore, the present invention provides easy to use means to grow and store cells in situ for testing methods. Indeed, the present invention makes viral, chlamydial and other diagnostic methods accessible to small laboratories, including those without cell culture capabilities.

11 Claims, No Drawings

IN SITU GROWTH, FREEZING AND TESTING OF CULTURED CELLS

FIELD OF THE INVENTION

The present invention provides methods and compositions for the in situ growth, freezing and testing of cultured cells. In particular, the present invention provides methods and compositions for the long-term preservation of cells in ready-to-use formats for testing. In addition, the present invention provides rapid and easy to use means to diagnose viral and other infections. Furthermore, the present invention provides easy to use means to grow and store cells in situ for testing methods. Indeed, the present invention makes viral, chlamydial and other diagnostic methods accessible to small laboratories, including those without cell culture capabilities.

BACKGROUND OF THE INVENTION

As intracellular parasites (e.g., viruses and Chlamydia) require living cells in order to replicate, diagnosis of infection due to these organisms relies upon the use of either animals (e.g., suckling mice), embryonated eggs, or cell cultures. As cell cultures are much less expensive and are easier to work with than animals or embryonated eggs, cell cultures have long been the mainstay of diagnosis methods for intracellular parasites and viruses in particular. Indeed, cell cultures are the foundation upon which a virology laboratory is built. These cultures may be produced in house from animal tissues or organs, or more commonly, purchased from commercial suppliers.

Regardless of their sources, cell cultures must be maintained over time, in order to ensure a ready supply of cells for growth and diagnosis of infections caused by intracellular parasites. In the laboratory, mammalian cells are routinely frozen in order to minimize the opportunity for contamination of the cultures, guard against handling errors that could result in the loss of the culture, and minimize the number of cell lines that must be handled on a daily basis. Frozen cell culture stocks are also useful for minimizing genetic drift and shift, senescence, and undesirable phenotypic changes that can occur when continuous and finite cell lines are cultured for long time periods.

Freezing methods have been developed to minimize the impact of osmotic shock and intracellular ice crystal formation, two factors that contribute to the loss of cell viability during freezing. Cryoprotectants such as glycerol and dimethylsulfoxide (DMSO) are commonly used to help prevent cell death during freezing. In addition to the use of cryoprotectants, traditional methods use slow cooling (approximately 1° C. per minute) until the cells reach a temperature of –25° C. Once this temperature is attained, the cells can be rapidly cooled to –70° C. or –196° C. (i.e., liquid nitrogen temperature), without further loss of cell viability. Omitting the cryoprotectant or rapid freezing causes the formation of intracellular ice crystals which can rupture cell membranes and result in cell death. By slowly cooling the cells, the external medium becomes supercooled and ice crystal nuclei form in the extracellular fluid. This results in an extracellular environment that contains an artificially elevated salt gradient which, in turn, causes an osmotic gradient. This gradient causes water to diffuse out of the cells and the nonelectrolyte cryoprotectants to diffuse into the cells. This "dehydration" of the cells tends to minimize osmotic shock and intracellular ice crystal formation. (See e.g., Wiedbrauk and Johnston, "Mammalian Cell Culture Procedures, in Manual of *Clinical Virology*, pages 33–44 [Raven Press, New York, 1993], for a description of these events).

However, commonly used freezing methods require specialized equipment and training. In addition, hazardous chemicals such as DMSO are typically used. Furthermore, thawing of frozen cells maintained in liquid nitrogen poses risks such as explosion of the vials or tubes as well as the danger of loss of cell viability due to improper handling (e.g., slow, rather than rapid thawing). Once the cells have been thawed, the freezing medium must be removed and rinsed from the cells and the culture revived prior to use for growth and/or detection of intracellular parasites. Once revived, the cultures are often placed into formats suitable for the detection and identification of viruses, including multiwell plates (e.g., microtiter plates), tubes, and slides). Thus, the cultures must be transferred from their growth flask to these other formats prior to their use. This necessitates additional equipment and personnel time, prior to the use of the cultures as desired. What is needed are cell cultures and methods that are easy to use, readily available, particularly in ready-to-use formats, require little operator time and/or experience to use, and are reliable.

SUMMARY OF THE INVENTION

The present invention provides methods and compositions for the in situ growth, freezing and testing of cultured cells. In particular, the present invention provides methods and compositions for the long-term preservation of cells in ready-to-use formats for testing. In addition, the present invention provides rapid and easy to use means to diagnose viral and other infections. Furthermore, the present invention provides easy to use means to grow and store cells in situ for testing methods. Indeed, the present invention makes viral, chlamydial and other diagnostic methods accessible to small laboratories, including those without cell culture capabilities.

The present invention provides methods for the detection of intracellular parasites in a sample, comprising the steps of providing a cell culture comprising cells, wherein the cell culture has been frozen and thawed in situ on a substrate, and a sample suspected of containing at least one intracellular parasite; adding the sample to the cell culture to produce an inoculated culture; incubating the inoculated culture under conditions such that the intracellular parasite infects the cells of the cell culture to produce an infected culture; and observing the infected culture for the presence of the intracellular parasite within the cells of the cell culture. In some embodiments, the substrate is selected from the group consisting of glass and plastic. In some preferred methods, the glass is a glass coverslip. In still other preferred embodiments, the plastic substrate is the well of a multiwell plate. In some embodiments, the intracellular parasite is selected from the group consisting of viruses and bacteria.

In some embodiments, the observing comprises observing for the presence of cytopathic effect, while in other embodiments, the observing comprises observing for the presence of fluorescent cells. In still other embodiments, the observing comprises observing for the presence of blue cells. In some preferred embodiments, multiple observations are made. For example, in some embodiments, observing for cytopathic effect is combined with observing for fluorescent cells, and/or observing for blue cells. As described herein, in preferred embodiments, the observing for fluorescent cells is accomplished using labeled antibodies that recognize an antigen (e.g., viral or bacterial) present in the culture (i.e., due to the infection of the cells by the virus(es) and/or bacteria). However, it is not intended that the present invention be limited to any particular fluorescence product, substrate, enzyme, or color. Indeed, it is intended that multiple antibodies and fluorescence labels will find use in some embodiments of the present invention. For example, it is contemplated that the cells of the present invention will be tested using multiple antibody preparations with differing fluorescent labels. In addition, it is not intended that the present invention be limited to fluorescently labeled antibodies, as other detection means will find use with the present invention. Also as described herein, the observing for blue cells is associated with test methods such as those that involve the use of a reporter gene which indicates that a particular gene is being expressed. However, it is not intended that the present invention be limited to any particular gene, product, substrate or color. Indeed, it is contemplated that the present invention will find use with multiple genes, products, substrates, and/or colors (i.e., multiple reporter genes will be used). Furthermore, in some particularly preferred embodiments, the use of fluorescent label(s) is combined with enzymatic method(s).

The present invention also provides methods for the detection of a toxin in a sample, comprising the steps of providing a cell culture comprising cells, wherein the cell culture has been frozen and thawed in situ on a substrate, and a sample suspected of containing at least one toxin; adding the sample to the cell culture to produce an inoculated culture; incubating the inoculated culture to produce an intoxicated culture; observing the intoxicated culture for the presence of cytopathic effect on the cells of the cell culture. In some embodiments, the substrate is selected from the group consisting of glass and plastic. In some preferred methods, the glass is a glass coverslip. In still other preferred embodiments, the plastic substrate is the well of a multiwell plate. In some preferred embodiments, the toxin is a Clostridium toxin, while in particularly preferred embodiments, the toxin is a Clostridium difficile toxin. However, it is not intended that the present invention be limited to Clostridium toxin. Indeed, it is intended that the present invention encompass the detection of various other toxins, including but not limited to verotoxins, mycotoxins, and other toxins of interest, in particular those that cause disease and/or pathological changes in a host upon exposure to the toxin. In addition, it is contemplated that the present invention will find use in detecting and/or identifying multiple toxins present in a single sample. It is also intended that the toxin(s) will be identified and/or detected using methods other than the observation and characterization of cytopathic effect. Thus, it is intended that the present invention encompasses the detection and/or identification of toxins using any suitable method, including but not limited to the use of antibodies, toxin substrate analogs, reporter genes, etc.

The present invention also provides methods for the production of frozen ready to use cell cultures for in situ diagnostic assays, comprising the steps of providing cells, and a substrate selected from the group consisting of glass and plastic; placing the cells on the substrate under conditions such that the cells are attached to the substrate to produce a cell monolayer; and freezing the cell monolayer under conditions such that the cell monolayer remains attached to the substrate. In some preferred embodiments the substrate is plastic, while in some particularly preferred embodiments, the plastic comprises the well of a multiwell plate. In still further preferred embodiments, the substrate is glass. In other preferred embodiments, the glass is a glass coverslip, and in particularly preferred embodiments, the glass coverslip is placed in a shell vial prior to freezing of the monolayer. The present invention also provides compositions comprising a cell monolayer produced according to these methods.

The present invention also provides methods for the detection of intracellular parasites in a sample, comprising the steps of providing the ready-to-use cell monolayer produced as described above, and sample suspected of containing at least one intracellular parasite; thawing the cell monolayer; adding the sample to the cell monolayer to produce an inoculated culture; incubating the inoculated culture under conditions such that the intracellular parasite infects the cells of the cell monolayer to produce an infected culture; and observing the infected culture for the presence of the intracellular parasite within the cells of the cell monolayer. In some embodiments, the intracellular parasite is selected from the group consisting of viruses and bacteria.

In some embodiments, the observing comprises observing for the presence of cytopathic effect, while in other embodiments, the observing comprises observing for the presence of fluorescent cells. In still other embodiments, the observing comprises observing for the presence of blue cells. In some preferred embodiments, multiple observations are made. For example, in some embodiments, observing for cytopathic effect is combined with observing for fluorescent cells, and/or observing for blue cells. As described herein, in preferred embodiments, the observing for fluorescent cells is accomplished using labeled antibodies that recognize an antigen (e.g., viral or bacterial) present in the culture (i.e., due to the infection of the cells by the virus(es) and/or bacteria). However, it is not intended that the present invention be limited to any particular fluorescence product, substrate, enzyme, or color. Indeed, it is intended that multiple antibodies and fluorescence labels will find use in some embodiments of the present invention. For example, it is contemplated that the cells of the present invention will be tested using multiple antibody preparations with differing fluorescent labels. In addition, it is not intended that the present invention be limited to fluorescently labeled antibodies, as other detection means will find use with the present invention. Also as described herein, the observing for blue cells is associated with test methods such as those that involve the use of a reporter gene which indicates that a particular gene is being expressed. However, it is not intended that the present invention be limited to any particular gene, product, substrate or color. Indeed, it is contemplated that the present invention will find use with multiple genes, products, substrates, and/or colors (i.e., multiple reporter genes will be used). Furthermore, in some particularly preferred embodiments, the use of fluorescent label(s) is combined with enzymatic method(s).

The present invention also provides methods for the detection of toxin in a sample, comprising the steps of providing a ready-to-use cell monolayer produced as described above, and a sample suspected of containing at least one toxin; adding the sample to the cell monolayer to produce an inoculated culture; incubating the inoculated culture to produce an intoxicated culture; and observing the intoxicated culture for the presence of cytopathic effect on the cells of the cell monolayer. In some embodiments, the toxin is a Clostridium toxin, while in particularly preferred embodiments, the toxin is a *Clostridium difficile* toxin. However, it is not intended that the present invention be limited to Clostridium toxin. Indeed, it is intended that the present invention encompass the detection of various other toxins, including but not limited to verotoxins, mycotoxins, and other toxins of interest, in particular those that cause disease and/or pathological changes in a host. In addition, it is contemplated that the present invention will find use in detecting and/or identifying multiple toxins present in a single sample. It is also intended that the toxin(s) will be identified and/or detected using methods other than the observation and characterization of cytopathic effect. Thus, it is intended that the present invention encompass the detection and/or identification of toxins using any suitable method, including but not limited to the use of antibodies, toxin substrate analogs, reporter genes, etc.

The present invention also provides compositions comprising frozen, ready-to-use cell culture suitable for the detection of pathogenic substances, wherein the pathogenic substances are selected from the group consisting intracellular parasites and toxins. In some embodiments, the intracellular parasites are selected from the group consisting of viruses and bacteria. In particularly preferred embodiments, the bacteria are members of the genus Chlamydia. In other embodiments, the toxin(s) comprises at least one Clostridium toxin, while in other preferred embodiments, the toxin is a *C. difficile* toxin.

DESCRIPTION OF THE INVENTION

The present invention provides methods and compositions for the in situ growth, freezing and testing of cultured cells. In particular, the present invention provides methods and compositions for the long-term preservation of cells in ready-to-use formats for testing. In addition, the present invention provides rapid and easy to use means to diagnose viral and other infections. Furthermore, the present invention provides easy to use means to grow and store cells in situ for testing methods. Indeed, the present invention makes viral, chlamydial and other diagnostic methods accessible to small laboratories, including those without cell culture capabilities.

The cell cultures of the present invention are frozen in a format that is ready for testing upon thawing of the cells. In particularly preferred embodiments, the cells are frozen on coverslips placed within vials (i.e., shell vials). In these embodiments, the cells are frozen on a glass substrate without the need for pre-starvation or any special handling of the cells prior to freezing. In addition, the cells do not require any special handling during thawing or use. Thus, the preparation of the ready-to-use cell cultures can be accomplished in an economical and cost-effective manner. This is unlike the methods currently available that require a starvation step and/or lengthy recovery of the cells following freezing (See e.g., U.S. Pat. No. 5,935,855, herein incorporated by reference). Thus, the present invention provides cells in a ready-to-use format that requires minimal handling both prior to the freezing and after the thawing of the monolayers. In addition to the preferred shell vial embodiments in which the cells are attached to a coverslip, the present invention provides cell monolayers attached to plastics (e.g., the plastic wells of multiwell plates), as well as cells directly attached to a glass substrate such as the glass of a vial.

This means that a laboratory can obtain frozen cell cultures in a desired format for testing, maintain the cultures in the freezer until they are needed, and then inoculate the thawed cultures as needed. Thus, the laboratory does not have to have the capability and funds available to maintain a cell culture service. For example, cells in the ready-to-use format of the present invention that are useful in the diagnosis of viral infections (e.g., respiratory viruses, herpes, etc.) may be removed from the freezer, thawed, inoculated, and the answer regarding the presence or absence of virus determined within a matter of hours or a few days. In addition, these frozen cells can be used to detect other intracellular parasites (e.g., Chlamydia), as well as the presence of microbial toxins (e.g., toxins produced by various species of Clostridium).

By providing cell cultures in a ready-to-use format, the need for the operator (i.e., the microbiologist or technologist) to transfer cells from growth flasks to slides, multiwell plates, or shell vials is avoided. In addition, the present invention avoids the necessity for using cell culture hoods and facilities. Indeed, the use of shell vials in particularly preferred embodiments minimizes the need for advanced training in virological methods, as well as the need for special incubators (e.g., $CO_2$ incubators commonly used with cell cultures), and space required to perform the tests. Shell vial inoculation, incubation, staining, and evaluation are relatively easy (See e.g., D. Leland, "Modified Virus Isolation Systems," in *Clinical Virology*, W. B. Saunders Co., Philadelphia, Pa. [1996], at pages 79–90). Although the vials require a special centrifuge carrier and a device to readily remove the coverslips from the bottom of the shell vials, the relative costs and inconvenience are small, as compared to the requirements of a typical cell culture laboratory. In addition, the use of shell vials can significantly shorten the times needed to make a diagnosis, and reduces the chances of contamination and/or deterioration of the cells, as compared to traditional cell culture methods. Thus, the present invention makes virology accessible to laboratories that are not equipped nor experienced with cell cultures.

Definitions

The terms "sample" and "specimen" in the present specification and claims are used in their broadest sense. On the one hand, they are meant to include a specimen or culture. On the other hand, they are meant to include both biological and environmental samples. These terms encompasses all types of samples obtained from humans and other animals, including but not limited to, body fluids such as urine, blood, fecal matter, cerebrospinal fluid (CSF), semen, sputum, and saliva, as well as solid tissue. These terms also refers to swabs and other sampling devices which are commonly used to obtain samples for culture of microorganisms.

Biological samples may be animal, including human, fluid or tissue, food products and ingredients such as dairy items, vegetables, meat and meat by-products, and waste. Environmental samples include environmental material such as surface matter, soil, water, and industrial samples, as well as samples obtained from food and dairy processing instruments, apparatus, equipment, disposable, and non-disposable items. These examples are not to be construed as limiting the sample types applicable to the present invention.

Whether biological or environmental, a sample suspected of containing microorganisms may (or may not) first be subjected to an enrichment means to create a "pure culture" of microorganisms. By "enrichment means" or "enrichment treatment," the present invention contemplates (i) conventional techniques for isolating a particular microorganism of interest away from other microorganisms by means of any culture medium and/or technique, and (ii) novel techniques for isolating particular microorganisms away from other microorganisms. It is not intended that the present invention be limited only to one enrichment step or type of enrichment means. For example, it is within the scope of the present invention, following subjecting a sample to a conventional enrichment means, to subject the resultant preparation to further purification such that a pure culture of a strain of a species of interest is produced. This pure culture may then be analyzed by the medium and method of the present invention.

As used herein, the term "organism" and "microorganism," are used to refer to any species or type of microorganism, including but not limited to viruses and bacteria, including rickettsia and chlamydia. Thus, the term encompasses, but is not limited to DNA and RNA viruses, as well as organisms within the orders Rickettsiales and Chlamydiales.

As used herein, the term "culture," refers to any sample or specimen which is suspected of containing one or more microorganisms. "Pure cultures" are cultures in which the organisms present are only of one strain of a particular genus and species. This is in contrast to "mixed cultures," which are cultures in which more than one genus and/or species of microorganism are present.

As used herein, the term "cell type," refers to any cell, regardless of its source or characteristics.

As used herein, the term "cell line," refers to cells that are cultured in vitro, including primary cell lines, finite cell lines, continuous cell lines, and transformed cell lines.

As used herein, the terms "primary cell culture," and "primary culture," refer to cell cultures that have been directly obtained from animal or insect tissue. These cultures may be derived from adults as well as fetal tissue.

As used herein, the term "finite cell lines," refer to cell cultures that are capable of a limited number of population doublings prior to senescence.

As used herein, the term "continuous cell lines," refer to cell cultures that have undergone a "crisis" phase during which a population of cells in a primary or finite cell line apparently ceases to grow, but yet a population of cells emerges with the general characteristics of a reduced cell size, higher growth rate, higher cloning efficiency, increased tumorigenicity, and a variable chromosomal complement. These cells often result from spontaneous transformation in vitro. Thuse cells have an indefinite lifespan.

As used herein, the term "transformed cell lines," refers to cell cultures that have been transformed into continuous cell lines with the characteristics as described above. Transformed cell lines can be derived directly from tumor tissue and also by in vitro transformation of cells with whole virus (e.g., SV40 or EBV), or DNA fragments derived from a transforming virus using vector systems.

As used herein, the term "hybridomas," refers to cells produced by fusing two cell types together. Commonly used hybridomas include those created by the fusion of antibody-secreting B cells from an immunized animal, with a malignant myeloma cell line capable of indefinite growth in vitro. These cells are cloned and used to prepare monoclonal antibodies.

As used herein, the term "mixed cell culture," refers to a mixture of two types of cells. In some preferred embodiments, the cells are cell lines that are not genetically engineered, while in other preferred embodiments the cells are genetically engineered cell lines. In some embodiments, the one or more of the cell types is re "permissive" (i.e., virus is capable of replication and spread from cell to cell within the culture). The present invention encompasses any combination of cell types suitable for the detection, identification, and/or quantitation of viruses in samples, including mixed cell cultures in which all of the cell types used are not genetically engineered, mixtures in which one or more of the cell types are genetically engineered and the remaining cell types are not genetically engineered, and mixtures in which all of the cell types are genetically engineered.

As used herein, the term "suitable for the detection of intracellular parasites," refers to cell cultures that can be successfully used to detect the presence of an intracellular parasite in a sample. In preferred embodiments, the cell cultures are capable of maintaining their susceptibility to infection and/or support replication of the intracellular parasite. It is not intended that the present invention be limited to a particular cell type or intracellular parasite.

As used herein, the term "susceptible to infection" refers to the ability of a cell to become infected with virus or another intracellular organism. Although it encompasses "permissive" infections, it is not intended that the term be so limited, as it is intended that the term encompass circumstances in which a cell is infected, but the organism does not necessarily replicate and/or spread from the infected cell to other cells. The phrase "viral proliferation," as used herein describes the spread or passage of infectious virus from a permissive cell type to additional cells of either a permissive or susceptible character.

As used herein, the term "toxin" refers to any substance (usually a protein or conjugated protein) that is detrimental (i.e., poisonous) to cells and/or organisms. In particularly preferred embodiments, the term refers to extracellular toxins produced by various bacterial species, including, but not limited to the members of the genus Clostridium. However, it is not intended that the present invention be limited to any particular toxin or bacterial species. Indeed, it is intended that the term encompass toxins produced by any organism.

As used herein, the terms "monolayer," "monolayer culture," and "monolayer cell culture," refer to cells that have adhered to a substrate and grow in as a layer that is one cell in thickness. Monolayers may be grown in any format, including but not limited to flasks, tubes, coverslips, wells of microtiter plates, roller bottles, etc. Cells may also be grown attached to microcarriers, including but not limited to beads. In particularly preferred embodiments, the monolayers of the present invention are grown on coverslips placed within shell vials.

As used herein, the term "suspension," and "suspension culture," refers to cells that survive and proliferate without being attached to a substrate. Suspension cultures are typically produced using hematopoietic cells, transformed cell lines, and cells from malignant tumors.

As used herein, the terms "culture media," and "cell culture media," refers to media that are suitable to support the growth of cells in vitro (i.e., cell cultures). It is not intended that the term be limited to any particular culture medium. For example, it is intended that the definition encompass outgrowth as well as maintenance media. Indeed, it is intended that the term encompass any culture medium suitable for the growth of the cell cultures of interest.

As used herein, the term "obligate intracellular parasite" (or "obligate intracellular organism) refers to any organism which requires an intracellular environment for its survival and/or replication. Obligate intracellular parasites include viruses, as well as many other organisms, including certain bacteria (e.g., most members of the orders Rickettsiales [e.g., Coxiella, Rickettsia and Ehrlichia] and Chlamydiales [e.g., *C. trachomatis, C. psittaci*], etc). The term "intracellular parasite," refers to any organism that may be found within the cells of a host animal, including but not limited to obligate intracellular parasites briefly described above. For example, intracellular parasites include organisms such as Brucella, Listeria, Mycobacterium (e.g., *M. tuberculosis* and *M. leprae*), and Plasmodium, as well as Rochalimea.

As used herein, the term "antimicrobial," is used in reference to any compound which inhibits the growth of, or kills microorganisms. It is intended that the term be used in its broadest sense, and includes, but is not limited to compounds such as antibiotics which are produced naturally or synthetically. It is also intended that the term includes compounds and elements that are useful for inhibiting the growth of, or killing microorganisms.

The terms "confluent" or "confluency" as used herein in reference to an adherent cell line define a condition wherein cells throughout a culture are in contact with each other creating what appears to be a continuous sheet or "monolayer" of cells.

The terms "cytopathic effect" or "CPE" as used herein describe changes in cellular structure (i.e., a pathologic effect) resulting from external agents such viruses and/or toxins. Common cytopathic effects include cell destruction, syncytia (i.e., fused giant cells) formation, cell rounding vacuole formation, and formation of inclusion bodies. CPE results from actions of a virus on permissive cells that negatively affect the ability of the permissive cellular host to preform its required functions to remain viable. In in vitro cell culture systems, CPE is evident when cells, as part of a confluent monolayer, show regions of non-confluence after contact with a specimen that contains a virus. The observed microscopic effect is generally focal in nature and the foci is initiated by a single virion. However, depending upon viral load in the sample, CPE may be observed throughout the monolayer after a sufficient period of incubation. Cells demonstrating viral induced CPE usually change morphology to a rounded shape, and over a prolonged period of time can die and be released form their anchorage points in the monolayer. When many cells reach the point of focal destruction, the area is called a viral plaque, which appears as a hole in the monolayer. Cytopathic effects are readily discernable and distinguishable by those skilled in the art.

As used herein, the term "substrate" refers to a physical support to which cells are capable of binding so as to produce a monolayer. In some embodiments, plastics are used as substrates for production and maintenance of monolayers, while in other preferred embodiments, glass is used as the substrate. However, it is not intended that the present invention be limited to any particular substrate.

As used herein, the term "glass" refers to the commonly used material. In particular, the term refers to hard, brittle, often transparent or translucent materials that are produced by fusing silicates with soda or potash, lime, and in some cases, various metallic oxides. In particularly preferred embodiments of the invention, type 2 glass is used. However, it is not intended that the present invention be limited to any particular type or formula of glass.

The term "multiwell" refers to any device that has multiple wells. In particularly preferred embodiments of the present invention plastic multiwell plates are used. These multiwell plates include, but are not limited to the two, four, eight, 16, 24, and 48 well plates commonly used in cell culturing methods, as well as microtiter plates (e.g., 96-well plates), and other suitable plate formats. It is not intended that the present invention be limited to any particular plate or number of wells. Indeed, it is contemplated that various multiwell plates will find use in the present invention.

The abbreviation "ONPG," represents o-Nitrophenyl-β-D-Galactopyranoside. ONPG is a substrate for the enzyme β-galactosidase (β-gal). The reaction between ONPG and β-gal produces a yellow product which can be quantified spectrophotometrically at 405 nm.

The abbreviation "X-gal," represents the chemical compound 5-bromo-4-chloro-3-indolyl-β-D-galactopyranoside, a substrate for the enzyme β-galactosidase. The reaction between X-gal and β-galactosidase results in the formation of a blue precipitate which is visually discernable.

The term "hybriwix," represents a product of Diagnostic Hybrids, Inc., Athens, Ohio which allows for quantification of certain viral DNA in an infected monolayer of cells by DNA hybridization. "DNA hybridization" is the annealing of two complementary DNA molecules whose base sequences match according to the rules of base pairing. DNA hybridization is used to identify or quantify an unknown or "target" DNA by hybridization to a known DNA or "probe." The probe is typically labeled with a reporter molecule such as $^{125}I$, a radioisotope which can be detected and quantified with a gamma counter.

The phrase "plaque reduction assay," or "PRA," as used herein describes a standard method used to determine efficacy of anti-viral drugs by enumerating a decrease in plaque formation in a cell monolayer exposed to a drug. A "plaque" is a defined area of "CPE." It is usually the result of infection of the cell monolayer with a single infectious virus which then replicates and spreads to adjacent cells of the monolayer. A plaque may also be referred to as a "focus of viral infection."

The term "permissive" as used herein describes the sequence of interactive events between a virus and its putative host cell. The process begins with viral adsorption to the host cell surface and ends with release of infectious virions. A cell is "permissive" if it readily permits the spread of virus to other cells. Many methods are available for the determination of the permissiveness of a given cell line, including, but not limited to plaque reduction assays, comparisons of the production and/or quantitation of viral proteins based on results obtained from gel electrophoresis, relative comparisons using hybridization analysis to analyze DNA or RNA content, etc.

The term "susceptible," as used herein describes the extent that a permissive or non-permissive host cell can adsorb and be penetrated by a virus. A cell line may be susceptible without being permissive in that it can be penetrated but not release virions. A permissive cell line however must be susceptible.

The phrase "seed on," as used herein describes the act of transferring an aqueous solution of suspended cells into a vessel containing cells adhered to a surface, after which the vessel is stored for a sufficient period of time to allow the suspended cells or "seeds" to settle out by gravity and attach in a relatively uniform manner to the adhered cells and become integrated into the final cell monolayer as a mixture. A "mixed cell monolayer," results from the "seed on" process.

The phrase "seed in," as used herein describes the mixing of two or more aqueous solutions of suspended tissue culture cells, each cell suspension having different cellular properties, and transfer of such mixture of cells into a vessel which is stored for a sufficient period of time to allow the suspended cells to settle out by gravity and attach in a relatively uniform manner such that the distribution of any single cell type is indicative of the relative ratio of the cells in the original mixture.

As used herein, the terms "chromogenic compound," and "chromogenic substrate," refer to any compound useful in detection systems by their light absorption or emission characteristics. The term is intended to encompass any enzymatic cleavage products, soluble, as well as insoluble, which are detectable either visually or with optical machinery. Included within the designation "chromogenic" are all enzymatic substrates which produce an end product which is detectable as a color change. This includes, but is not limited to any color, as used in the traditional sense of "colors," such as indigo, blue, red, yellow, green, orange, brown, etc., as well as fluorochromic or fluorogenic compounds, which produce colors detectable with fluorescence (e.g., the yellow-green of fluorescein, the red of rhodamine, etc.). It is intended that such other indicators as dyes (e.g., pH) and luminogenic compounds be encompassed within this definition.

As used herein, the commonly used meaning of the terms "pH indicator," "redox indicator," and "oxidation-reduction indicator," are intended. Thus, "pH indicator," encompasses all compounds commonly used for detection of pH changes, including, but not limited to phenol red, neutral red, bromthymol blue, bromcresol purple, bromoresol green, bromchlorophenol blue, m-cresol purple, thymol blue, bromcresol purple, xylenol blue, methyl red, methyl orange, and cresol red. The terms "redox indicator," and "oxidation-reduction indicator," encompasses all compounds commonly used for detection of oxidation/reduction potentials (i.e., "eH") including, but not limited to various types or forms of tetrazolium, resazurin, and methylene blue.

As used herein, the term "inoculating suspension," or "inoculant," is used in reference to a suspension which may be inoculated with organisms to be tested. It is not intended that the term "inoculating suspension," be limited to a particular fluid or liquid substance. For example, inoculating suspensions may be comprised of water, saline, or an aqueous solution. It is also contemplated that an inoculating suspension may include a component to which water, saline or any aqueous material is added. It is contemplated in one embodiment, that the component comprises at least one component useful for the intended microorganism. It is not intended that the present invention be limited to a particular component.

As used herein, the term "kit," is used in reference to a combination of reagents and other materials.

As used herein, the term "primary isolation," refers to the process of culturing organisms directly from a sample. As used herein, the term "isolation," refers to any cultivation of organisms, whether it be primary isolation or any subsequent cultivation, including "passage," or "transfer," of stock cultures of organisms for maintenance and/or use.

As used herein, the term "presumptive diagnosis," refers to a preliminary diagnosis which gives some guidance to the treating physician as to the etiologic organism involved in the patient's disease. Presumptive diagnoses are often based on "presumptive identifications," which as used herein refer to the preliminary identification of a microorganism.

As used herein, the term "definitive diagnosis," is used to refer to a final diagnosis in which the etiologic agent of the patient's disease has been identified. The term "definitive identification" is used in reference to the final identification of an organism to the genus and/or species level.

The term "recombinant DNA molecule," as used herein refers to a DNA molecule which is comprised of segments of DNA joined together by means of molecular biological techniques.

The terms "reporter gene construct," or "reporter gene vector," as used herein refers to a recombinant DNA molecule containing a sequence encoding the product of a reporter gene and appropriate nucleic acid sequences necessary for the expression of the operably linked coding sequence in a particular host organism. Eukaryotic cells are known to utilize promoters, enhancers, and termination and polyadenylation signals.

The term "reporter gene," refers to an oligonucleotide having a sequence encoding a gene product (typically an enzyme) which is easily and quantifiably assayed when a construct comprising the reporter gene sequence operably linked to a heterologous promoter and/or enhancer element is introduced into cells containing (or which can be made to contain) the factors necessary for the activation of the promoter and/or enhancer elements. Examples of reporter genes include but are not limited to bacterial genes encoding β-galactosidase (lacZ), the bacterial chloramphenicol acetyltransferase (cat) genes, firefly luciferase genes and genes encoding β-glucuronidase (GUS).

The term "genetically engineered cell line," refers to a cell line that contains heterologous DNA introduced into the cell line by means of molecular biological techniques (i.e., recombinant DNA technology).

The term "stable transfection," or "stably transfected," refers to the introduction and integration of foreign DNA into the genome of the transfected cell. The term "stable transfectant," refers to a cell which has stably integrated foreign DNA into the genomic DNA.

The term "stable transfection" (or "stably transfected"), refers to the introduction and integration of foreign DNA into the genome of the transfected cell. The term "stable transfectant," refers to a cell which has stably integrated foreign DNA into the genomic DNA.

The term "selectable marker," as used herein refers to the use of a gene which encodes an enzymatic activity that confers resistance to an antibiotic or drug upon the cell in which the selectable marker is expressed. Selectable markers may be "dominant"; a dominant selectable marker encodes an enzymatic activity which can be detected in any mammalian cell line. Examples of dominant selectable markers include the bacterial aminoglycoside 3' phosphotransferase gene (also referred to as the neo gene) which confers resistance to the drug G418 in mammalian cells, the bacterial hygromycin G phosphotransferase (hyg) gene which confers resistance to the antibiotic hygromycin and the bacterial xanthine-guanine phosphoribosyl transferase gene (also referred to as the gpt gene) which confers the ability to grow in the presence of mycophenolic acid. Other selectable markers are not dominant in that their use must be in conjunction with a cell line that lacks the relevant enzyme activity. Examples of non-dominant selectable markers include the thymidine kinase (tk) gene which is used in conjunction with tk⁻cell lines, the CAD gene which is used in conjunction with CAD-deficient cells and the mammalian hypoxanthine-guanine phosphoribosyl transferase (hprt) gene which is used in conjunction with hprt⁻cell lines. A review of the use of selectable markers in mammalian cell lines is provided in Sambrook et al. (Sambrook et al., supra at pp.16.9–16.15).

Experimental

The following examples are provided in order to demonstrate and further illustrate certain preferred embodiments and aspects of the present invention and are not to be construed as limiting the scope thereof.

In the experimental disclosure which follows, the following abbreviations apply: eq (equivalents); M (Molar); μM (micromolar); N (Normal); mol (moles); mmol (millimoles); μmol (micromoles); nmol (nanomoles); g (grams); mg (milligrams); μg (micrograms); ng (nanograms); pg (picograms); l or L (liters); ml (milliliters); μl (microliters); cm (centimeters); mm (millimeters); μm (micrometers); nm (nanometers); xg (times gravity);° C. (degrees Centigrade); FBS (fetal bovine serum); PBS (phosphate buffered saline; HEPES (N-[2-hydroxyethyl]piperazine-N'-[2-ethanesulfonic acid]); HBSS (Hank's Balanced Salt Solution); MEM (Minimal Essential Medium); EMEM (Eagle's Minimal Essential Medium); DMSO (dimethyl sulfoxide); ELVIS® RM (ELVIS® Replacement Medium); PFU (plaque forming unit); TNTC (too numerous to count); FITC (fluorescein isothiocyanate); Lee Laboratories (Lee Laboratories, Grayson, Ga.); ELVIS® (enzyme-linked virus inducible system) HSV cells; CDT (Clostridium difficile toxin); Diagnostic Hybrids (Diagnostic Hybrids, Inc., Athens, Ohio); Promega (Promega, Corporation, Madison, Wis.); Kimble (Kimble/Kontes, Vineland, N.J.); Bellco (Bellco Glass Inc., Vineland, N.J.); Costar (Acton, Mass.); Falcon (Franklin Lakes, N.J.); Chemicon (Chemicon, Inc., Temecula, Calif.); BBL (Becton Dickinson Microbiology Systems, Cockeysville, Md.); DIFCO (Difco Laboratories, Detroit, Mich.); U.S. Biochemical (U.S. Biochemical Corp., Cleveland, Ohio); Chemicon (Chemicon, Inc., Temecula, Calif.); Fisher (Fisher Scientific, Pittsburgh, Pa.); Sigma (Sigma Chemical Co., St. Louis, Mo.); ATCC (American Type Culture Collection, Rockville, Md.); Bartel's (Bartel's, Issaquah, Wash.); and BioWhittaker (BioWhittaker, Walkersville, Md.).

The cells used during the development of the present invention and described in the following Examples, were obtained from the ATCC, with the exception being that the BGMK and PRMK cells were obtained from BioWhittaker, and the MRC-5 cells were obtained from both ATCC and BioWhittaker. The ATCC numbers of the cells are indicated in the following Table.

TABLE 1

ATCC Cell Lines

| Cell Line | ATCC Number |
| --- | --- |
| BHK/ICP6LacZ-5 | CCL-12072 |
| A549 | CCL-185 |
| CV-1 | CCL-70 |
| HEp-2 | CCL-23 |
| hs27 | HFF; CRL-1634 |
| Mv1Lu | CCL-64 |
| McCoy | CCL-1696 |
| NCI-H292 | CCL-1848 |
| MRC-5 | CCL-171 |
| WI-38 | CCL-75 |
| Vero | CCL-81 |
| MDCK (NBL-2) | CCL-34 |
| BHK21 | CCL-10 |
| HEL299 | CCL-137 |
| HeLa | CCL-2 |

EXAMPLE 1

Growth and Freezing of R-Mix Cells

In this Example, the growth and freezing of R-Mix (Mixed FreshCells™ from Diagnostic Hybrids) in situ on a glass coverslip placed into a dram vial (shell vial) is described.

R-Mix is a mixture of mink lung cells (Mv1Lu) and human adenocarcinoma cells (A549). The cells were grown separately to confluency in cell culture flasks, trypsinized and diluted in cell culture medium to an optical density of (absorbance at 500 nm) of 0.014 for A549 cells and 0.008 for mink lung cells, and then mixed together by adding an equal volume of each cell suspension. Then, 0.75 ml of this mixed cell suspension was subsequently transferred to a sterile one dram glass vial (Kimble, USP type 1 glass) containing a sterile, circular glass coverslip (12–13 mm in diameter; Bellco, USP type 2 glass). The vials were stored briefly on a level surface at ambient temperature to allow the cells to settle out uniformly by gravity. Once the cells were attached (usually requiring less than 1 hour), the vials were moved to an incubator at 35–37° C., in order to allow the cells to grow into a confluent mixed cell monolayer within 3–4 days post-planting. The cell growth medium was gently aspirated from the dram vial without disturbing the cell monolayer and 0.5 ml of freezing medium (90% calf serum, 10% DMSO) was added by pouring the medium down the side of the vial to minimize disturbance of the cell sheet. No starvation step was conducted. The vials were transferred to a styrofoam freezing pack and the pack was placed into a −85° C. freezer, until use.

EXAMPLE 2

Thawing of R-Mix Cells on Glass Coverslips

In this Example, experiments in which R-Mix™ cell cultures frozen on a glass coverslip in a shell vial were retrieved from the freezer and thawed without losing cells viability. The vials were transferred from the −85° C. freezer directly to a 35–37° C. water bath, wherein the fluid in the water bath was adequate to meet the level of the freeing medium in the vial. Within 3–4 minutes, the medium went from frozen to completely aqueous. During this thawing period, the vials should not be moved or jostled because the "ice crystals" formed during freezing can cause abrasions to the monolayer if the crystal contacts the cell surface as the crystal "phase" of the medium dissolves. Once thawed, the freezing medium was removed by gentle aspiration and 1 ml of pre-warmed RM-03T replacement medium (Diagnostic Hybrids) compatible with R-Mix™ cells was used to rinse the cells. This medium was then removed by gentle aspiration and an additional 1 ml of RM-03T was added. The cell cultures were incubated for a brief time (approximately 4 hours), the medium changed one more time (RM-03T was used), and 0.2 ml of each diluted, stock laboratory respiratory virus isolates (influenza A, influenza B, adenovirus, respiratory syncytial virus [RSV], parainfluenza 1, parainfluenza 2, and parainfluenza 3) were inoculated. Virus dilutions were performed to ensure virus inocula between 10 to 10,000 PFUs of a particular virus in any vial. The R-Mix™ vial was centrifuged at 700 xg for 60 min at ambient temperature and the vial placed in the incubator at 35–37° C., for 22–24 hrs or longer, if needed to obtain reliable results. The cells were stained with a FITC-labeled monoclonal antibody (Chemicon) directed against the virus isolates tested.

EXAMPLE 3

Infection of Frozen and Thawed R-Mix™ Cell Cultures

In this Example, fresh as well as frozen and thawed R-Mix™ cell cultures prepared as described in Examples 1 and 2 were infected with stock respiratory viruses (listed in Table 2 below), in order to determine whether the cells are susceptible to viral infection and can be used for diagnosis of viral infection. The viruses and the viral quantities were variable, based on varied dilutions performed on each virus isolate. The cells were fixed by first aspirating the medium and then adding 0.25 ml of fixing solution (80% acetone/ 20% water) to each monolayer. After 1–5 minutes incubation, the fixing solution was aspirated and 0.2 ml of the respective FITC-labeled monoclonal antibody was added to the monolayers. The vials were stoppered and incubated for 30 minutes at 35–37° C. The coverslips were removed from the shell vials, carefully rinsed in water and placed cell side down on a drop of buffered glycerol mounting medium on a glass slide. The number of fluorescent cells in each monolayer was counted with the aid of a fluorescence microscope set for FITC. The results obtained after fixing and staining are shown in the following Table. These experiments were done in duplicate. When the number of organisms used was large, the designation "TNTC" is used in the Table to indicate that five microscopic fields were counted for each of two coverslips; an average per filed count is indicated as well. In this Table, "field" is based on 100X magnification. The values obtained for the frozen/ thawed cells were compared with those obtained with the fresh cells (i.e., the standard of reference).

TABLE 2

Comparison of Fresh and Frozen/Thawed R-Mix ™ Cultures for the Culture/Detection of Respiratory Viruses

| Virus | Fresh (Non-Frozen) | Frozen/Thawed |
|---|---|---|
| Influenza A | TNTC (approx. 21/field) | TNTC (approx. 40/field) |
| Influenza B | 22, 26 | 38, 50 |
| Adenovirus | 25, 18 | 25, 50 |
| Respiratory Syncytial Virus | 10, 10 | 9, 10 |
| Parainfluenza 1 | 237, 238 | 442, 400 |
| Parainfluenza 2 | TNTC (approx. 16/field) | TNTC (approx. 14/field) |
| Parainfluenza 3 | Approx. 10/field | Approx. 25/field |

It is apparent from the above Table that all cases, the frozen/thawed preparation of R-Mix™ was substantially equivalent to the fresh, non-frozen cell preparations of R-Mix™, in detecting the panel of respiratory viruses used in these experiments.

EXAMPLE 4

Growth and Freezing of ELVIS® HSV Cells

In this Example, the growth, freezing and use of ELVIS® HSV cells (Diagnostic Hybrids) was tested. These cells were grown in situ on a glass coverslip placed in a 1 dram vial (i.e., shell vial). ELVIS® HSV cells (BHK/ICP6LacZ cells) were grown to confluency in cell culture flasks, trypsinized and diluted in cell culture medium to an optical density (absorbance at 500 nm) of 0.034. Then, 0.75 ml of this cell suspension was transferred to a sterile one dram glass vial (Kimble, USP type 1 [borosilicate] glass) containing a sterile, circular glass coverslip (12–13 mm in diameter; Bellco, USP type 2 [soda lime] glass). The vials were stored briefly on a level surface at ambient temperature to allow the cells to settle out uniformly by gravity. Once the cells were attached, (usually requiring less than 1 hour), the vials were moved to an incubator at 35–37° C., in order to allow the cells to grow into a confluent cell monolayer within 3–4 days post-planting. The cell growth medium was gently aspirated from the dram vial without disturbing the cell monolayer and 0.5 ml of freezing medium (90% calf serum, 10% DMSO) was carefully added down the side of the vial to minimize disturbance of the cell sheet. No starvation step was necessary. The vials were transferred to a styrofoam freezing pack and the pack was placed into a –85° C. freezer for storage until use.

EXAMPLE 5

Thawing and Testing of ELVIS® HSV Cells on Glass Coverslips

In this Example, ELVIS® HSV cell cultures frozen on glass coverslips in shell vials were thawed and tested. Vials containing ELVIS® HSV cell cultures frozen on glass coverslips prepared as described in Example 4, were retrieved from the –85° C. freezer and transferred directly to a 35–37° C. water bath with the water level sufficient to meet the level of the freeing medium in the vial. Within 3–4 minutes, the medium went from frozen to completely aqueous. During this thawing period, the vials were not be moved or jostled because the "ice crystal" can cause abrasions to the monolayer if the crystal contacts the cell surface as the crystal "phase" of the medium dissolves. Once thawed, the freezing medium was removed by gentle aspiration and 1 ml of pre-warmed replacement medium ELVIS® RM (Diagnostic Hybrids) compatible with ELVIS® HSV cells was used to rinse the cells. The medium was removed by gentle aspiration and an additional 1 ml of fresh ELVIS® RM was added. Laboratory virus stocks of HSV-1 and HSV-2 (originally obtained from specimen isolates) were diluted to approximately 250 PFU/ml, and 0.2 ml of these dilutions were immediately used to inoculate the cells (i.e., unlike the R-Mix cells which required a 4 hour incubation of the cells prior to inoculation with virus).

The inoculated ELVIS® HSV vial was centrifuged at 700xg for 60 min at ambient temperature and the vial placed in the incubator at 35–37° C. for at least 22–24 hours. The cells were stained for herpes-specific induction of the genetically engineered β-galactosidase reporter gene present in these proprietary cells using an ELVIS® HSV Staining Kit (Diagnostic Hybrids). Cell monolayers were inspected for positive, blue staining ELVIS® HSV cells using an inverted light microscope with a total magnification of 100X. Monoclonal antibody directed against specific types of herpes virus may also be used in the staining buffer or subsequent to staining for the β-galactosidase reporter gene. The results are described in Example 6, below.

EXAMPLE 6

Infection of Frozen and Thawed ELVIS® HSV Cell Cultures

In this Example. frozen and thawed, as well as control (i.e., fresh) ELVIS® HSV cells were infected with laboratory stock cultures of herpes virus (HSV-1 and HSV-2), as described in Example 5 above. These experiments were conducted in triplicate. The cells were tested using the ELVIS® HSV ID/Typing Test Kit (Diagnostic Hybrids). Briefly, after the incubation period (See, Example 5), the medium was carefully aspirated from the vials and 0.25 ml of fixing solution (80% acetone/20% water) was added to the monolayers. After 1–5 minutes of fixing, the fixing solution was carefully aspirated and 0.25 ml of Solution 2 (containing x-gal, two FITC-labeled monoclonal antibodies directed against HSV-2, and two unlabeled monoclonal antibodies directed against HSV-1) were added to each monolayer. The monolayers were then incubated for 60 minutes. After this incubation period, the monolayers were examined for the presence of blue cells (i.e., those infected by HSV). Next, the coverslips were carefully removed from the shell vials, rinsed in water, and placed cell side down on a drop of buffered glycerol mounting medium and examined for fluorescent cells.

During the incubation of Solution 2 with the HSV-infected monolayer, the x-gal is hydrolyzed by the HSV-induced β-galactosidase to form a blue precipitate inside the cells. The blue cells can be detected using a light microscope and the fluorescence can be detected by using a fluorescence microscope. Thus, cells infected with HSV-2 are recognized by the FITC-labeled monoclonal antibodies to HSV-2; these cells appear blue and fluoresce. However, if the cells are infected with HSV-1, blue cells are observed but there will be no fluorescence detected when the cells are examined under a fluorescent microscope, as the cells will be recognized by the unlabeled monoclonal antibodies directed against HSV-1. In order to visualize the binding of HSV-1 and these antibodies under a fluorescent microscope, the monolayers were treated with Solution 3 (containing FITC-labeled goat anti-mouse antibody). Thus, in order to confirm the presence of HSV-1, the coverslips were removed from the slide, rinsed in water and placed cell side down on a drop of Solution 3 and incubated for 15 minutes at 35–37° C. The coverslips were then rinsed in water, placed cell side down on a drop of buffered glycerol and examined using a fluorescence microscope.

The results for both blue staining cells and cells fluorescing with type-specific monoclonal antibodies are shown in the following Table.

TABLE 3

Infection of ELVIS ® HSV Cells With HSV

| Virus | Number of Positive Fresh ELVIS ® HSV Cells | | Number of Positive Frozen ELVIS ® HSV Cells | |
|---|---|---|---|---|
| | β-Gal Positive | Antibody Positive | β-Gal Positive | Autibody Positive |
| HSV-1 | 40 ± 4 | 10 ± 1 | 81 ± 3 | 38 ± 8 |
| HSV-2 | 73 ± 4 | 58 ± 7 | 14 ± 1 | 20 ± 2 |

The results in Table 3 seem to indicate that frozeii/thawed cells may lead to a greater demonstration of infection, particularly with HSV-1. However, the fact that the cells are required to recover from a stressed condition may allow the virus an advantage in infecting and replicating in these stressed cells. Thus, these cells may provide an indication of greater infection levels at earlier post-inoculation times.

EXAMPLE 7

Clinical Evaluation of Frozen and Fresh ELVIS® HSV Cells

In this Example, frozen and freshly prepared ELVIS® HSV cells were tested with clinical specimens. In these experiments, clinical specimens were split (i.e., the sample was divided up into portions for distribution) between a clinical virology laboratory and a small, rural microbiology with little to no tissue cell culture and/or viral culture experience. In these experiments, the performance of ELVIS® HSV cells for rapid HSV detection in a clinical virology laboratory (VL) at a teaching hospital using fresh (F) and in situ frozen (ISF) formats was compared to the performance of ELVIS® HSV cells in a rural, small hospital microbiology laboratory (ML) using only the more practical ISF format. These experiments showed that use of in situ freezing of ELVIS® HSV cells is a practical alternative for prolonged storage of cells on site, making rapid herpes testing feasible in all clinical microbiology labs.

ELVIS® HSV cells were grown to confluent monolayers on glass coverslips in dram vials using EMEM, 7% FBS with pen/strep (100 units penicillin and 100 μg/ml streptomycin). After removing this growth medium, 0.5 ml of freezing medium (90% heat-inactivated calf serum and 10% DMSO) were added and the cells frozen at –85° C. The cells were then provided on dry ice or shipped to the laboratories at ambient temperature to simulate routine practice. IFS cultures were rapidly thawed at 35–37° C. in a water bath. The shipping medium was removed from all cultures and replaced with 1 ml cell culture medium (ELVIS® RM; Diagnostic Hybrids).

Fifty clinical specimens from patients suspected of having genital herpes were collected, divided into matched samples, frozen and provided to VL, and ML test sites. When the cells were ready to be inoculated, 0.2 ml specimen were used for inoculation and all cultures were centrifuged for 60 min at 700 xg and incubated for 16–24 hrs. Monolayers were fixed for 2 min. using 0.25 ml Solution 1 cell fixative (80% acetone in water; Diagnostic Hybrids) and histochemically stained for 60 min at 35–37° C. to detect HSV-induced β-galactosidase, a reporter gene construct engineered into ELVIS® cells, using the ELVIS® HSV Staining Kit (Diagnostic Hybrids), per the manufacturer's instructions. Monolayers were observed for blue, HSV-infected cells with a light microscope at 100x magnification; HSV-positive monolayers were subsequently typed using fluorescent-labeled, HSV type-specific monoclonal antibodies and fluorescent microscopy. At VL, 24 specimens were found to be HSV positive (11 HSV-1; 13 HSV-2) and 26 specimens were HSV negative in both F and ISF ELVIS® formats. There was no discernible reduction in the ELVIS® detection signal (i.e. number of blue stained cells), between the two cell culture formats.

Using the ISF format only, and in blinded fashion, ML identified the same specimens as HSV positive and HSV negative as did VL. Furthermore, the type identity of each HSV positive specimen concurred 100% between VL and ML. First, no difference was observed between ELVIS® HSV cells provided fresh or frozen in situ. These data suggest that the need to purchase cells each week could be replaced by bulk purchase of cells frozen in situ and ready for immediate use upon rapid thawing. Second, there was 100% agreement between results derived from an experienced virology laboratory and those results from a small microbiology laboratory that had never performed a cell culture-based or herpes culture test previous to this study.

EXAMPLE 8

Growth and Freezing of ELVIS® HSV Cells in situ in Polystyrene Multiwell Plates

In this Example, the growth and freezing of ELVIS® HSV cells in situ within the wells of polystyrene multiwell plates was investigated. ELVIS® HSV cells were grown to confluency in cell culture flasks, trypsinized and diluted in EMEM with 7% FBS and pen/strep (100 units/ml penicillin and 100 μg/ml streptomycin) medium to an optical density (absorbance at 500 nm) of 0.028. Then, 0.75 ml of the cell suspension was subsequently transferred to individual wells of a 24 well plate (Costar or Falcon). The plate was stored briefly on a level surface at ambient temperature to allow the cells to settle out uniformly by gravity. Once the cells attached (usually requiring less than 1 hour), the multiwell plates were moved to a 35–37° C. incubator with a humidified chamber and 5% $CO_2$, in order to grow into a confluent cell monolayer within 3–4 days post-planting. The cell growth medium was gently aspirated from each well without disturbing the cell monolayer and 0.5 ml of freezing medium (90% calf serum, 10% DMSO) was carefully added, by pouring it down the side of each well to minimize disturbance of the cell sheet. No starvation step was found to be necessary. The vials were transferred to a styrofoam freezing pack and the pack was placed into a –85° C. freezer until use.

EXAMPLE 9

Thawing and Testing of ELVIS® HSV Cells in Polystyrene Multiwell Plates

In this Example, frozen ELVIS® HSV cell cultures in multiwell plates prepared as described in Example 8, were retrieved from the freezer and thawed in the following manner. The plates were transferred from the –85° C. freezer directly to a dry heating device set at approximately 35–37° C., designed so that it made direct contact with the surface of the cold niultiwell plate. Within 25 minutes, the medium went from frozen to completely aqueous. During this thawing period, the plates were not be moved or jostled because the "ice crystal" can cause abrasions to the monolayer if the crystal contacts the cell surface as the crystal "phase" of the medium dissolves. Once thawed, the freezing medium was removed by gentle aspiration and 1 ml of pre-warmed replacement medium ELVIS® RM (Diagnostic Hybrids) were used to rinse the cells. This medium was removed by gentle aspiration and an additional 1 ml of ELVIS® RM was added. Laboratory stock viruses of HSV-1 and HSV-2 (same as used in the previous Examples) (0.2 ml each) were inoculated immediately (i.e., unlike the R-Mix cells, for which it was determined that for optimum performance, a 4 hour incubation is required prior to inoculation). The samples were incubated as described above, and then tested as described in Example 10, below.

EXAMPLE 10

Infection of Fresh and Frozen/Thawed ELVIS® HSV Multiwell Cell Cultures with Laboratory Stock Herpes Virus Cultures In this Example, frozen and thawed ELVIS® HSV cells in multiwell plates prepared as described in Example 8 and 9 were inoculated with herpesvirus cultures to determine the susceptibility of the cells to viral infection.

Serial two-fold dilutions of HSV-1 and HSV-2 laboratory stocks of known titer were prepared and 0.2 ml of each dilution (500, 250, 125, 67, 33, and 16 PFU/ml) of each virus was tested using a frozen/thawed ELVIS® HSV cells prepared in a multiwell plate and fresh. In addition, control cells (fresh ELVIS® HSV cells) in multiwell plates were also tested. After the addition of the viral dilutions to each cell culture system, the inoculated plates were centrifuged at 700 xg for 60 min at ambient temperature and the placed in the incubator at 35–37° C. for at least 22–24 hours.

The cells were stained for herpes-specific induction of the genetically engineered β-galactosidase reporter gene present in these proprietary cells using an ELVIS® HSV Staining Kit (Diagnostic Hybrids). Cell monolayers were inspected for positive, blue staining ELVIS® HSV cells using an inverted light microscope with a total magnification of 100X. The number of blue stained cells for each run (these tests were run in duplicate is recorded in the Tables below, with the expected number of blue stained cells indicated in parentheses. The expected number of blue-stained cells was based on a determination using standard viral titration methods on fresh, non-frozen ELVIS® HSV cells.

TABLE 4

Number of Positive Frozen/Thawed ELVIS ® Cells

| Virus | Dilution (PFU/ml) | | | | | |
|---|---|---|---|---|---|---|
| | 500 | 250 | 125 | 67 | 33 | 16 |
| HSV-1 | 95, 106 (100) | 60, 60 (50) | 34, 25 (25) | 9, 24 (12) | 2, 5 (6) | 1, 1 (3) |
| HSV-2 | 89, 89 (100) | 44, 55 (50) | 23, 21 (25) | 17, 9 (12) | 3, 8 (6) | 3, 1 (3) |

TABLE 5

Number of Positive Fresh ELVIS ® Cells

| Virus | Dilution (PFU/ml) | | | | | |
|---|---|---|---|---|---|---|
| | 500 | 250 | 125 | 67 | 33 | 16 |
| HSV-1 | 58, 53 (100) | 16, 32 (50) | 11, 8 (25) | 7, 6 (12) | 0, 3 (6) | 0, 2 (3) |
| HSV-2 | 116, 131 (100) | 59, 52 (50) | 30, 27 (25) | 15, 14 (12) | 5, 9 (6) | 2, 3 (3) |

EXAMPLE 11

Growth and Freezing Human Foreskin Fibroblast Cells

In this Example, human foreskin fibroblast cells (HFF; Diagnostic Hybrids) were grown and frozen in situ on a glass coverslip placed into a dram vial (shell vial). HFF cells were grown to confluency in cell culture flasks, trypsinized and diluted in EMEM with 10% FBS and gentamicin (10 $\mu$g/ml) to an optical density (absorbance, at 500 nm) of 0.020. The cell suspension was transferred to a sterile one dram glass vial (Kimble, USP type 1 glass) containing a sterile, circular glass coverslip (12–13 mm in diameter; Bellco USP type 2 glass). The vials were stored briefly on a level surface at ambient temperature to allow the cells to settle out uniformly by gravity. Once the cells attached (usually requiring less than 1 hour), the vials were moved to a 35–37° C. incubator, and allowed to grow into a confluent cell monolayer (3–4 days). The cell growth medium was gently aspirated from the dram vial without disturbing the cell monolayer and 0.5 ml of freezing medium (90% calf serum, 10% DMSO) was carefully added by pouring it down the side of the vial to minimize disturbance of the cell sheet. No starvation step was found to be necessary. The vials were transferred to a styrofoam freezing pack and the pack was placed into a –85° C. freezer until use.

EXAMPLE 12

Thawing of HFF Cells on Glass Coverslips

In this Example, HFF cells prepared as described in Example 11 were thawed and tested. Frozen HFF cell cultures on glass coverslips shell vials were retrieved from the freezer and thawed in the following manner. The vials were transferred from the −85° C. freezer directly to a 35–37° C. water bath, with a water level that met the level of the freeing medium in the vial. Within 3–4 minutes, the medium went from frozen to completely aqueous. During this thawing period, the vials were not be moved or jostled because the "ice crystal" can cause abrasions to the monolayer if the crystal contacts the cell surface as the crystal "phase" of the medium dissolves. Once thawed, the freezing medium was removed by gentle aspiration and 1 ml of pre-warmed replacement medium RM-02 (Diagnostic Hybrids) compatible with HFF cells was used to rinse the cells. This medium was removed by gentle aspiration and an additional 1 ml of RM-02 added. The specimen (0.2 ml) was inoculated immediately (i.e., unlike the R-Mix cells where a 4 hour incubation was found to be required prior to inoculation). In these experiments, the samples were *Clostridium difficile* toxin (CDT; Lee Laboratories) in combination with anti-toxin, and anti-toxin alone. The antitoxin used in these experiments was obtained from a *C. difficile* toxin kit (Bartel's). The CDT concentration ranged from $10^6$ pg/ml to $10^0$ pg/ml in a serial, 10-fold dilution profile. The samples were then re-incubated for up to 48 hours. Cell monolayers were inspected for the appearance of cytotoxicity in the non-neutralized samples, and inhibition of *C. difficile*-specific cytotoxicity in the neutralized samples. Both fresh (non-frozen) and frozen/thawed cells were able to detect (as indicated by cytotoxicity), the presence of non-neutralized CDT at $10^6$ pg/ml, $10^5$ pg/ml, $10^4$ pg/ml, $10^3$ pg/ml, $10^2$ pg/ml, and $10^1$ pg/ml. Neither the fresh nor frozen/thawed cells were able to detect cytotoxicity at the $10^0$ pg/ml level of CDT.

EXAMPLE 13

Comparison of Glass Coverslips and Vials as Growth Substrates

In this Example, preliminary experiments to test glass coverslips and shell vials were tested for their relative ability to allow the successful in situ growth and use of frozen cells were conducted. These results indicated that conditions that promote good results with cells on coverslips do not promote good results on shell vials alone. Indeed, in these experiments, a wide variety of cell types and cells derived from human and non-human sources were planted on both glass shell vials + glass coverslips versus glass vials alone. The cell lines included single cell monolayers, mixed cell line monolayers, and genetically engineered cell monolayers. The cells were inoculated onto coverslips and shell vials at suitable concentrations (i.e., to produce a confluent monolayer of approximately 200,000 to 400,000 cells), and incubated at approximately 35–37° C. The results are shown in the following Table. In this Table, "4+" indicates that the monolayers were in very good condition, while "3+" indicates that the cells were in good condition. In some cases, holes of varying sizes were observed in the monolayer (i.e., there were areas in which no cells were present, ranging from small gaps in the monolayer sheet to large holes). In some cases, multiple holes in the monolayer were observed. Notably, while the ELVIS® HSV cells on the shell vial did not initially appear very healthy post thawing, the cells recovered and produced a good monolayer after overnight incubation. For the tests with E-Mix A cells, it appears that one cell line did not survive the process very well. However, these data are based on only one experiment and may have been an aberrant result.

TABLE 6

Growth of Cell Monolayers on Shell Vials With and Without Coverslips

| Cell Monolayers | Shell Vial with Coverslip: Appearance Post-Thawing | Shell Vial with Coverslip: Appearance After Overnight Incubation | Shell Vial Without Coverslip: Appearance Post-Thawing | Shell Vial Without Coverslip: Appearance After Overnight Incubation |
|---|---|---|---|---|
| Mv1Lu | 4+ | 4+ | Small gaps | 4+ |
| H292 | 4+ | 4+ | 4+ | 4+ |
| MRC-5 | 4+ | 4+ | Large holes | 4+ |
| HEp-2 | 4+ | 4+ | 4+ | 3+ |
| McCoy | 4+ | Many dead cells | 4+ | Mostly dead cells |
| ELVIS ® | 4+ | 4+ | Many holes | 4+, recovered |
| MDCK | 4+ | 4+ | 4+ | 4+ |
| LLCMK2 | 4+ | Cells dying | 4+ | Cells dying |
| HeLa | 4+ | Lot of dying cells | 4+ | Lot of dying cells |
| HFF | 4+ | 4+ | 4+ | 4+ |
| BGMK | 4+ | Few dead cells | 4+ | Few dead cells |
| A549 | 4+ | 4+ | 4+ | 4+ |
| H&V Mix (CV1/MRC-5) | 4+ | 4+ | Small gaps | 4+ |
| R-Mix | 4+ | 4+ | 4+ | 4+ |
| E-Mix A (RD/H292) | 4+ | One cell line poor | Holes | One cell line poor |
| E-Mix B (BGMK/A549) | 4+ | 4+ | 4+ | 4+ |
| MDCK/Mv1Lu | 4+ | 4+ | 4+ | 4+ |

EXAMPLE 14

Growth and Freezing Chinese Hamster Ovary Luciferase Cells

In this Example, CHO/Luc (Diagnostic Hybrids) cells were tested using the methods described above for other cell types. These CHO cells transfected with the human thyroid stimulating hormone receptor and the reporter gene luciferase were grown and frozen in the wells of polystyrene multiwell plates.

CHO/Luc cells were grown in 96 well plates for a one-day level of confluence in Ham's F-12 medium with 10% FBS (without antimicrobials) (CHO/Luc Solution 1 Growth Medium; Diagnostic Hybrids). The cell culture medium was removed and the cells treated with 80 $\mu$l per well freezing medium (90% calf serum, 10% DMSO). The plates were placed in styrofoam containers in a −80° C. freezer until use.

EXAMPLE 15

Thawing of CHO/Luc Cells in Polystyrene Multiwell Plates

In this Example, CHO/Luc cells prepared as described in Example 14 were thawed and tested. The plates containing frozen CHO/Luc cells were thawed in a 35–37° C. incubator for 10 minutes, and then washed twice with CHO Solution 1 Growth Medium (Diagnostic Hybrids). Then, 100 $\mu$l per well of CHO Solution 1 was added to each well, and the monolayers were allowed to recover overnight in a 35–37° C. incubator. These cells were then used to identify patients with autoantibodies directed against the human TSH receptor.

The thawed and recovered cells were stimulated for four hours with 10 $\mu$l of IgG samples (10 mg/ml) that were resuspended in a pool of 90 µl normal serum. The cells were lysed with Promega Lysis Buffer (Promega Corp) and the luciferase production was measured using the Promega Luciferase Assay System (Promega). In addition to the frozen/thawed cells, control (fresh) cells were also The results are shown in the following Table. In this Table, the results are shown as a percentage above a normal pool serum. A correlation coefficient of 0.62 was used. A patient positive for human TSH receptor autoantibodies is identified when the percent reactivity exceeds 130% of that of the normal pooled serum. Patients 18, 19, 22, 23, and 25 were determined to be positive in methods using both fresh and frozen/thawed CHO/Luc cells, while patient 24 was negative for TSH autoantibodies using both fresh and frozen/thawed CHO/Luc cells. These results indicate that frozen/thawed CHO/Luc cells are suitable for use in determinations of autoimmune diseases such as Graves' disease.

TABLE 7

Autoantibodies Against Human TSH Receptor

| Patient Sample Number | Frozen % Above Normal | Fresh % Above Normal |
|---|---|---|
| 18 | 138 | 141 |
| 19 | 134 | 136 |
| 22 | 149 | 171 |
| 23 | 190 | 178 |
| 24 | 130 | 121 |
| 25 | 197 | 186 |

EXAMPLE 16

Use of Frozen/Thawed McCoy Cells

In this Example, the use of frozen and thawed McCoy cells is described for detection and diagnosis of infection by *Chlamydia trachomatis*. McCoy cells are prepared, frozen and thawed in shell vials as described above for other cell cultures. After thawing, the medium is carefully aspirated from the monolayer and 0.5 ml HBSS used to rinse the monolayer. Then, 0.2 ml of specimen (or control) in Chlamydia Isolation Medium (EMEM, 10% FBS, 10 µg/ml gentamicin, 1 µg/ml cycloheximide, and 2 mM glutamine) suspension are added to the monolayers. The shell vials are centrifuged for 60 minutes at 1000 xg. Then, 0.8 ml Chlamydia Isolation Medium is added to each monolayer and the cultures allowed to incubate for 2 days at 35–37° C. The medium is then aspirated and the monolayers fixed as described in the previous Examples. The fixation medium is aspirated and 0.2 ml of a monoclonal antibody (FITC-labeled anti-Chlamydia antibody) added. The monolayers are incubated for 30 minutes at 35–37° C. The coverslips are carefully removed from the shell vials and placed cell side down on a drop of buffered glycerol mounting medium on a microscope slide. The cells are then examined for fluorescent inclusions.

In summary, the present invention provides numerous advances and advantages over the prior art, including providing a simple, rapid, easy-to-use means to diagnose viral and other infections. In addition, the present invention provides an easy to use means to grow and store cells in situ for testing methods. Indeed, the present invention makes viral, chlamydial and other diagnostic methods accessible to small laboratories, including those without cell culture capabilities. All of these advantages enhance the speed and accuracy of determining test results in diagnostics.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in diagnostic virology, cell culture, and/or related fields are intended to be within the scope of the following claims.

What is claimed is:

1. A method for the detection of at least one intracellular parasite in a sample, comprising the steps of:
    a) providing:
        i) a cell culture comprising cells, wherein said cell culture has been frozen and thawed in situ on a substrate, wherein the in situ frozen and thawed cells detect at least one intracellular parasite, and
        ii) a sample suspected of containing at least one intracellular parasite;
    b) adding said sample to said cell culture, to produce an inoculated culture;
    c) incubating said inoculated culture under conditions such that said intracellular parasite infects said cells of said cell culture to produce an infected culture; and
    d) observing said infected culture for the presence of said intracellular parasite within the cells of said cell culture.

2. The method of claim 1, wherein said substrate is selected from the group consisting of glass and plastic.

3. The method of claim 2, wherein said glass is a glass coverslip.

4. The method of claim 2, wherein said plastic substrate is the well of a multiwell plate.

5. The method of claim 1, wherein said intracellular parasite is selected from the group consisting of viruses and bacteria.

6. The method of claim 1, wherein said observing comprises observing for the presence of cytopathic effect.

7. The method of claim 1, wherein said observing comprises observing for the presence of fluorescent cells.

8. The method of claim 1, wherein said observing comprises observing for the presence of blue cells.

9. The method of claim 1, wherein said cells are frozen when confluent.

10. The method of claim 1, wherein said cells are not exposed to said parasite prior to in situ freezing and thawing.

11. The method of claim 1, wherein said cells are BHK/ICP6LacZ cells, said parasite is herpes simplex virus-1, and wherein said in situ frozen and thawed BHK/ICP6LacZ cells have 2 to 3.8 fold higher sensitivity to said herpes simplex virus-1 compared to BHK/ICP6LacZ cells which are not in situ frozen and thawed.

* * * * *